(12) United States Patent  
Kaplan et al.

(10) Patent No.: US 12,050,253 B2  
(45) Date of Patent: Jul. 30, 2024

(54) NON-DESTRUCTIVE TEST FIXTURE FOR SCREENING ELECTRICAL CONTINUITY

(71) Applicant: GALVANI BIOELECTRONICS LIMITED, Stevenage (GB)

(72) Inventors: Ellen Kaplan, Brentford (GB); Cindy Au, Brentford (GB); Pey-Jiun Ko, Brentford (GB)

(73) Assignee: GALVANI BIOELECTRONICS LIMITED, Stevenage (GB)

(*) Notice: Subject to any disclaimer, the term of this patent is extended or adjusted under 35 U.S.C. 154(b) by 197 days.

(21) Appl. No.: 17/594,924

(22) PCT Filed: May 1, 2020

(86) PCT No.: PCT/US2020/030954  
§ 371 (c)(1),  
(2) Date: Nov. 3, 2021

(87) PCT Pub. No.: WO2020/227066  
PCT Pub. Date: Nov. 12, 2020

(65) Prior Publication Data  
US 2022/0206083 A1    Jun. 30, 2022

Related U.S. Application Data

(60) Provisional application No. 62/843,217, filed on May 3, 2019.

(51) Int. Cl.  
*G01R 31/08* (2020.01)  
*G01R 1/067* (2006.01)  
(Continued)

(52) U.S. Cl.  
CPC ......... *G01R 31/54* (2020.01); *G01R 1/06705* (2013.01); *G01R 1/06794* (2013.01); *A61N 1/0553* (2013.01); *A61N 1/0556* (2013.01)

(58) Field of Classification Search  
CPC ............ G01R 1/06705; G01R 1/06794; G01R 31/54; G01R 31/58; A61N 1/0553; A61N 1/0556; A61N 1/08  
See application file for complete search history.

(56) References Cited

U.S. PATENT DOCUMENTS

| | | | |
|---|---|---|---|
| 4,857,857 A * | 8/1989 | Valenti | G01R 31/52 324/555 |
| 5,396,181 A | 3/1995 | O'Brien et al. | |

(Continued)

FOREIGN PATENT DOCUMENTS

WO    2019/020983 A1    1/2019

OTHER PUBLICATIONS

Search Report for European Patent Application No. 20801588.3 (Dec. 7, 2022).

(Continued)

*Primary Examiner* — Thang X Le  
(74) *Attorney, Agent, or Firm* — Merchant & Gould P.C.

(57) ABSTRACT

A test fixture (20) for testing continuity in at least one electrode of a neuromodulation device. The test fixture may comprise a substrate (22), at least one electrically conductive pad (24a) disposed on the substrate for reducing pressure applied to the at least one electrode when the electrically conductive pad makes contact with an exposed surface of the electrode, and a wire (26a) extending from the at least one electrically conductive pad. The pad may be formed of a non-abrasive material, such as conductive foam or smooth metal. The substrate may be a probe formed with a number of slots for holding pads and routing wires, a mandrel with openings for holding pads and routing wires, and a flexible circuit with exposed smooth metal surfaces. The test fixture may be suitable for testing cuff-like and paddle-like devices.

21 Claims, 5 Drawing Sheets

(51) Int. Cl.
    *G01R 31/54*          (2020.01)
    *A61N 1/05*           (2006.01)

(56) References Cited

U.S. PATENT DOCUMENTS

| | | |
|---|---|---|
| 5,552,713 A | 9/1996 | Rashidi |
| 2001/0025192 A1* | 9/2001 | Gerber ................. A61N 1/0551 607/117 |
| 2005/0182466 A1 | 8/2005 | Mahajan |
| 2010/0106204 A1* | 4/2010 | Moffitt ..................... A61N 1/37 600/300 |
| 2010/0145222 A1* | 6/2010 | Brunnett .................. A61B 5/05 600/554 |
| 2010/0192374 A1* | 8/2010 | Maschino ............ A61N 1/0551 29/882 |
| 2014/0303703 A1 | 10/2014 | Mercanzini et al. |
| 2016/0331960 A1 | 11/2016 | Katnani et al. |
| 2017/0203098 A1 | 7/2017 | Jiang et al. |
| 2019/0001133 A1 | 1/2019 | Onarheim et al. |
| 2019/0001135 A1 | 1/2019 | Yoo et al. |
| 2019/0094281 A1 | 3/2019 | Foeger et al. |

OTHER PUBLICATIONS

International Search Report and Written Opinion for PCT/US2020/30954 (Aug. 19, 2020).

* cited by examiner

NON-DESTRUCTIVE TEST FIXTURE FOR SCREENING ELECTRICAL CONTINUITY

PRIORITY CLAIM

The present application is a National Phase entry of PCT Application No. PCT/US2020/030954, filed May 1, 2020, which claims priority from U.S. Provisional Application No. 62/843,217, filed May 3, 2019, each of which is hereby fully incorporated herein by reference.

TECHNICAL FIELD

The disclosure relates generally to the field of electrodes, and more particularly to electrodes employed in the field of neuromodulation. Still more particularly, but not exclusively, the disclosure relates to a test fixture including a non-abrasive conductive material to test the electrodes of a neural interface.

BACKGROUND

Electrodes are often susceptible to damage with conventional continuity measurement methods, such as using a multimeter and probes to measure the DC resistance across the electrodes. In the field of bioelectronic medicine, to test lead functionality and the continuity of electrodes post-manufacturing and before implantation in a patient, the leads need to be adequately tested for DC resistance without damaging the electrode surface. A current method of using a multimeter with probes to measure electrode-to-electrode resistance, which may potentially cause damage to the electrode surface, is unsuitable because it could compromise the functionality of the lead.

SUMMARY

The present disclosure addresses the foregoing problem by providing an inventive method and fixture to allow electrode continuity to be checked while protecting the electrode surface from damage. According to an illustrative embodiment, the electrodes are placed in contact with a non-abrasive conductive material (e.g., conductive foam or a smooth conductive pad) that provides electrical continuity to test points that are measurable via traditional means (e.g., using a digital multimeter and probes). Exemplary implementations are depicted in the drawings.

According to an embodiment, there is provided a test fixture (20) for testing electrical continuity in an electrode (17) of a neuromodulation device (10), comprising a substrate (22), an electrically conductive pad (24) disposed on the substrate and sized relative to the electrode for reducing pressure applied to the electrode when the electrically conductive pad makes contact with an exposed surface of the electrode, and a conductive wire (26) extending from the electrically conductive pad.

The electrically conductive pad may be sized relative to at least one electrode to reduce pressure applied to the at least one electrode when the electrically conductive pad makes contact with an exposed surface of the electrode.

The pressure is reduced when the conductive pad makes contact with a surface of the electrode compared to when a single point contact is made with a surface of the electrode. For example, such a single point contact may be made when using a traditional probe.

In an illustrative embodiment, a test fixture comprises a plurality of non-abrasive electrically conductive pads connected to a first wire and a second wire, respectively, and each positioned to make contact with a separate corresponding electrode of a neuromodulation device, such as cuff, which includes finger portions supporting the electrodes. The first and second wires are configured to be electrically coupled to the probes of a multimeter for performing electrical continuity testing of the electrodes.

In an embodiment, the non-abrasive conductive pads are formed of a conductive foam that provides a normal force against the electrodes when slightly compressed to establish and maintain electrical contact between the non-abrasive conductive pads and the electrodes. In an embodiment, the non-abrasive conductive pads are formed around the circumference of an oversized mandrel (52) to ensure better electrical contact between the non-abrasive conductive pads and the electrodes. In an embodiment, the non-abrasive conductive pads are formed from exposed metal on a flex circuit and wrapped around the oversized mandrel with pressure sensitive adhesive. In an embodiment, a clamping tool (70) may be used to apply pressure around the exterior of the neuromodulation device to ensure sufficient electrical contact between the non-abrasive conductive pads and the electrodes. In an embodiment, the neuromodulation device is a substantially flat paddle device (80) and a clamping tool may be used to apply pressure to either or both of the non-abrasive conductive pads and the flat paddle device to ensure contact between the non-abrasive conductive pads and the electrodes.

According to an embodiment, there is provided a test fixture for testing electrical continuity in an electrode of a neuromodulation device, comprising: a substrate; an electrically conductive portion disposed on the substrate, wherein the substrate comprises a probe configured for the neuromodulation device to wrap around such that the electrically conductive portion is in contact with the electrode; and a wire extending from the electrically conductive portion. In other words, the substrate comprises a probe around which the neuromodulation device at least partly wraps. The probe may be generally cylindrical for the neuromodulation device to at least partly wrap around the probe.

For example, where the neuromodulation device comprises a cuff-like configuration, the probe enables the electrical continuity test to be carried out with less manipulation of the neuromodulation device (or neural interface device). Furthermore, there is reduction of handling of the neuromodulation device itself (and thus any potential damage to the neuromodulation device) as the neuromodulation device also is not required to be opened up excessively.

The disclosed solution uses a combination of materials and methods to generate electrical continuity from a soft, functionally-sensitive-to-scratching surface to harder, uncritical-to-performance test points that can withstand repeated electrical probing. The disclosed embodiment is suitable for electrodes that are coated or textured via laser-patterning or another surface morphology modification method such as nano-imprinting resulting in a surface integrity that needs to be protected to ensure the coating or texture's functional performance. Using non-abrasive conductive material to transfer electrical signals from the electrode surface to less-fragile test points protects the functionality of the electrodes, and leads, thus allowing for pre-implantation screening of the leads. Possible alternative embodiments may employ different materials to contact the electrodes, and different methods of generating continuity between the non-abrasive material and the test points.

DETAILED DESCRIPTION OF THE DRAWINGS

The disclosure relates to systems and devices for testing the continuity of electrodes in neuromodulation devices configured to stimulate nerves intra- or extra-venously when implanted in a body. The neuromodulation devices may include one or more electrodes positioned at different locations within cuff-like or paddle-like devices that may be implanted in a body such that the electrodes are in contact with surface tissue including nerves. Stimulation of the nerves may be defined by the delivery of electricity (e.g., electrical pulses) to a neuron, a nerve cell, a nerve bundle, or other target location of the nervous system that excites the neuron, nerve cell, nerve bundle, or other target location. Such electrical pulses may be generated by, for example, an implantable pulse generator (IPG) or an external pulse generator. The neuromodulation device referred to herein does not necessarily include such a pulse generator, and may also be referred to as a neural interface device.

Figure 1:
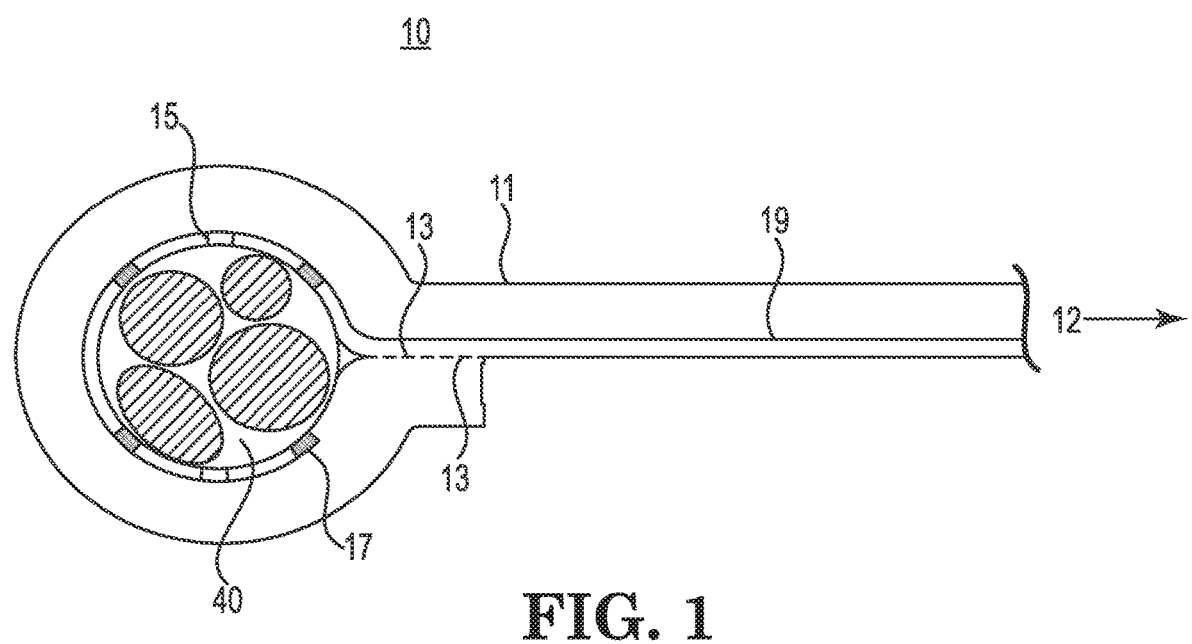
FIG. 1 is a cross-sectional view of an example of an implantable neuromodulation device cuffed about a nerve bundle.

FIG. 1 depicts an exemplary neuromodulation device 10 solely for the purpose of providing context for the present disclosure and is not intended to limit the scope of the disclosure herein. The neuromodulation device 10 depicted in FIG. 1 is a cuff-like device formed of a flexible, biocompatible material 11, such as a soft polymer substrate suitable for implantation within a body. The implantable device 10 may be used to stimulate a nerve using energy generated from a voltage induced in the implantable device by a source 12 (not otherwise shown in FIG. 1). As shown, the implantable device 10 is an extra-vascular device wrapped around a nerve or blood vessel 40 and joined together at points 13. The implantable device 10 is merely exemplary and may come in many different shapes, configurations, sizes, etc.

The implantable device 10 may include one or more electrodes 17 or arrays of electrodes. Some of the electrodes may be sensors 15 that receive rather than transmit electrical fields. In some embodiments, each electrode 17 may be configured to emit electrical fields to stimulate a nerve 40 proximate to the implantable device 10. The electrodes 17 may be individually wired and controlled or wired and controlled as an array. In some embodiments, each electrode may reflect a micro-electrode designed for maximum charge injection for stimulating a nerve.

Each electrode within an electrode 17 (or an array of such electrodes, etc.) may be coupled individually or to one another via a high-density, flexible interconnection 19 made substantially out of conductive material. In some embodiments, for example, interconnection 19 may be comprised substantially (e.g., 90 or 95 percent by weight) out of metals such as platinum, stainless steel, tungsten or titanium. Other metals, such as gold, may also be used for interconnection 19. As depicted in FIG. 1, the electrodes 17 may be connected via interconnection 19 in series and/or in parallel to provide multiple channels for increased selectivity of the parameters of the emitted electric field (e.g., magnitude, direction, location, etc.). In some embodiments, this arrangement may provide for more targeted and efficient stimulation of a nerve.

The electrodes 17 may be coupled to one or more other components of implantable device 10 for conducting processes consistent with the disclosed embodiments. These couplings may occur through interconnection 19, couplings made from the same or similar materials, or other couplings electrically linking the coupled components. In some embodiments, for instance, the electrode array 17 and/or its component sets of electrodes or individual electrodes may be coupled to a control circuit, a battery, capacitive storage and/or other chargeable storage elements to emit an electric field to stimulate a proximate nerve in response to a control signal received from the control circuit.

The one or more sensors 15, which may also be electrodes or arrays of electrodes, may measure a physical or temporal parameter associated with implantable device 10 and/or its surroundings. For example, in one embodiment, the set of sensors 15 may include sensors for measuring the electrical potential between two points. In addition, the set of sensors 15 may include other sensors for measuring other characteristics such as pressure, temperature, time, resistance, conductance, electrical/magnetic flux, and so forth. Each sensor in the set of sensors 15 may be coupled to any other component of implantable device 10, such as the control circuit, electrode arrays 17, energy sources, etc.

Each of the components of implantable device 10 may be formed within or affixed into the soft polymer substrate 11 so that the substrate supports the formed or affixed components. In certain embodiments, the substrate 11 may comprise a single piece of flexible polymer material, such as silicone, to facilitate implantation into a patient and manipulation therein. In some embodiments, the substrate 11 may comprise a plurality of layers of material with various components, such as electrodes 17, sensors 15 and interconnection 19 positioned between the layers. The resulting implantable device 10 may be flat, substantially flat, partially rounded, fully rounded, etc.

The small size of the electrodes, wires and welds in neuromodulation devices makes them difficult to manufacture. The flexibility of the devices also makes them prone to damage from handling. It is therefore desirable to test the continuity of the electrodes of neuromodulation devices before implantation. The traditional manner of testing continuity involves the use of a digital multimeter and one or more conductive metal probes that contact the surface of the electrodes. The hard, pointed, abrasive tip of the probe, as well as its concentrated pounds per square inch of pressure, can result in damage to the surface of the electrode.

The present disclosure comprises several embodiments for addressing problems associate with traditional continuity testing. In one embodiment, further illustrated in FIGS. 2A and 2B, a non-abrasive conductive material formed as pads are used in place of the probes. As used herein, the term "pad" refers to a piece of material shaped and sized in a manner similar to that of the electrodes to be tested. If an electrode is placed in a recessed portion of a neuromodulation device, the pad may need to be smaller than the electrode in order to make full contact with the exposed surface of the electrode. In neuromodulation devices where the electrodes protrude slightly from the surface of the device, the pad may be smaller or larger than the electrode. A larger surface area for the pad may serve to reduce the amount of pressure that can be exerted by the pad on the electrode.

The manner in which the electrodes are electrically wired to the digital multimeter may depend on the manner in which the electrodes of the neuromodulation device are wired. As used herein, the term "wire" refers to any type of material that may be used to connect one conductive device to another and may include any type of conductor, whether a solid wire, a flat trace or lead, etc. If the electrodes of the neuromodulation device are individually wired, then the corresponding wires of the pads of the test fixture may be individually wired. If some of the electrodes of the neuromodulation device are wired in series or parallel, the pads of the test fixture may be similarly wired. In one example in which the pads of the neuromodulation device are interconnected, a continuity test may be based on a continuity loop that goes from a digital multimeter point A, to a wire A, to pad A, to electrode A to an interconnection coil within the neuromodulation device to electrode pad B, to pad B, to wire B to digital multimeter point B. If the digital multimeter has enough channels and test points, it may be possible to test all of the electrodes of the neuromodulation device at the same time. In other situations, it may be necessary to test one set of electrodes, then move the neuromodulation device to test a next set of electrodes. Even a single pad may be used to test a single electrode in a monopolar configuration provided there is another conduction point at the other end of the monopolar device (i.e., a lead in the wiring harness of the neuromodulation device).

The pads may be formed of a variety of conductive materials. In an embodiment, the material used to form the contact surface of the pads is non-abrasive. As used herein, "non-abrasive" refers to the material having a lower hardness and/or roughness than that of the surface of the electrode. In an embodiment, the contact surface material of the pad is a conductive foam, such as Condus Plus™ made by Rogers Corporation, which is made of a low-density microcellular urethane with a thin, flexible metalized coating. The conductive foam may be formed on a substrate of any suitable shape, size and configuration and wired as appropriate for the neuromodulation device to be tested. Wiring may be run under each of the conductive foam pads and directly welded to the pads. The foam pads may also be positioned over and connected to other conductive materials that are then connected to the required wiring and substrate.

In some embodiments, the electrically conductive pad may comprise other shapes and therefore may be referred to as electrically conductive portion.

Figure 2A:
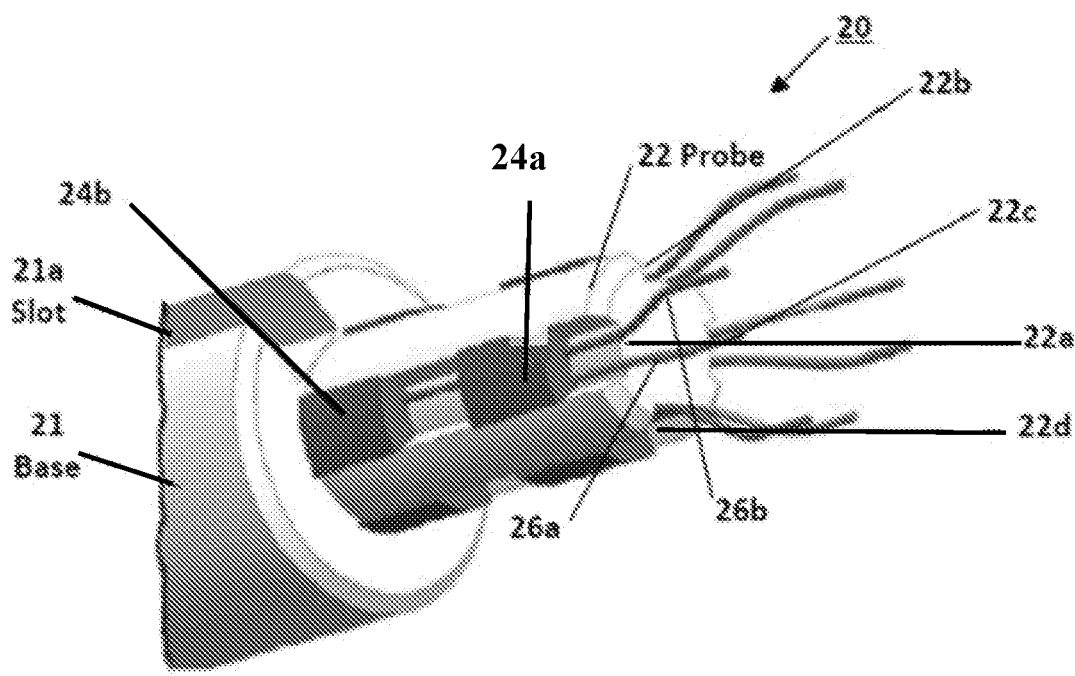
FIGS. 2A and 2B are perspective views of an embodiment of the inventive test fixture without and with a neuromodulation cuff.
Figure 2B:
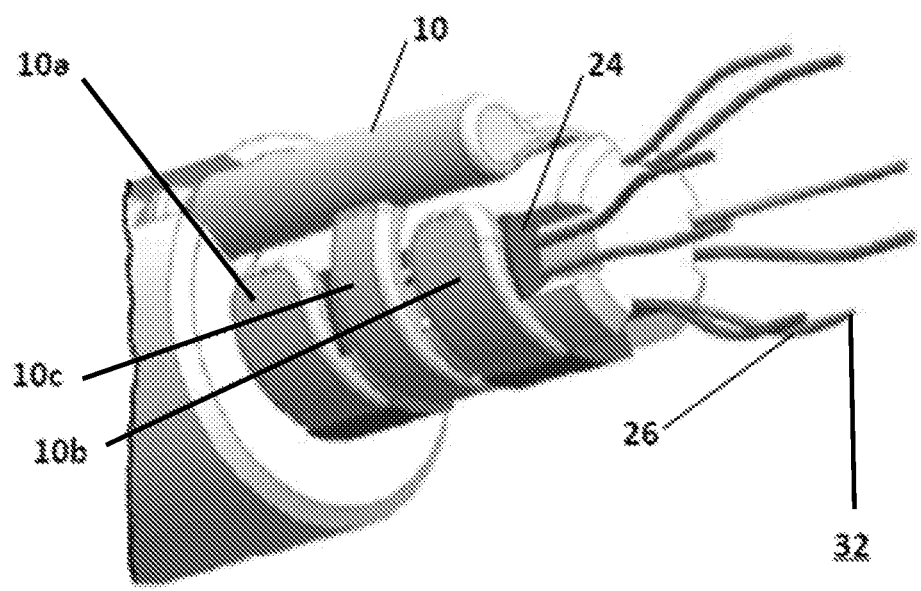

In the embodiment of the test fixture 20 illustrated in FIGS. 2A and 2B, the substrate for the conductive foam pads includes a base 21 comprising a first cylindrical portion, in which a base portion slot 21a is formed, and a probe 22 extending from the base. The slot 21a is not essential but positioning the lead of the neuromodulation device 10 in the slot may help to positionally align (i.e., clock) the neuromodulation device 10 relative to the test fixture 20. The probe comprises a second cylindrical portion having walls forming a plurality of probe slots 22a, 22b, 22c, 22d. The probe slots 22a, 22b, 22c and 22d are likewise not essential but do help to hold the pads 24a and 24b in position and provide a routing path for the wires 26.

A first non-abrasive electrically conductive pad 24a formed of conductive foam is disposed within a first probe slot 22a, and a first wire 26a extends from the first pad. In addition, a second non-abrasive electrically conductive pad 24b formed of conductive foam is disposed within the first probe slot 22a, and a second wire 26b extends from the second pad. The probe, probe slots, and pads are configured to accept a neuromodulation device 10. In an embodiment, when the neuromodulation device is positioned around the probe 20 and pads 24, the conductive foam may be slightly compressed. As a result, the spring force of the slightly compressed pads may provide a normal force so as to better establish electrical conductivity between the pads and the electrodes.

As previously described, the neuromodulation device may have a number of different shapes and sizes that are suitable for use with the embodiment of the test fixture 20. As illustrated, the neuromodulation device is a cuff-like device that includes a number of flexible finger portions 10a, 10b and 10c. As illustrated, the flexible fingers 10a and 10b include electrodes that are positioned to make contact with the pads 24a and 24b. The flexible finger 10c does not include any electrodes and is positioned in-between the pads 24a and 24b. As indicated at reference numeral 32, the wires 26 are configured to be electrically coupled to probes of a digital multimeter (not shown) for electrical continuity testing.

Figure 3A:
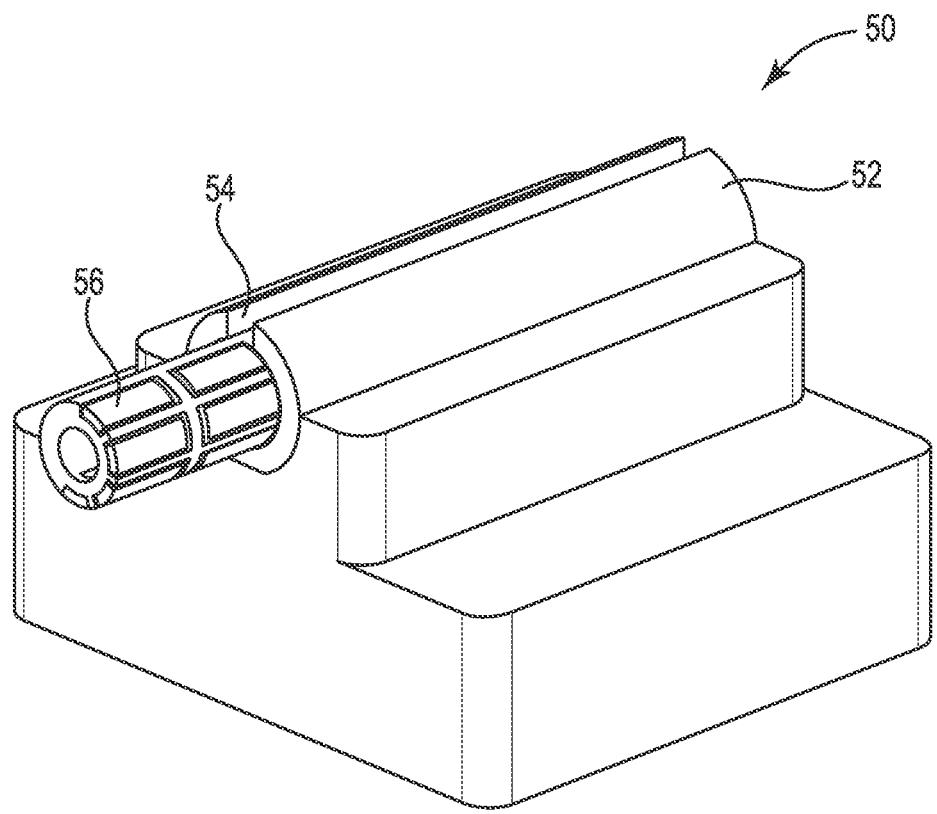
FIGS. 3A and 3B are perspective views of an embodiment of the inventive test fixture positioned around a mandrel with wire routing paths built therein.
Figure 3B:
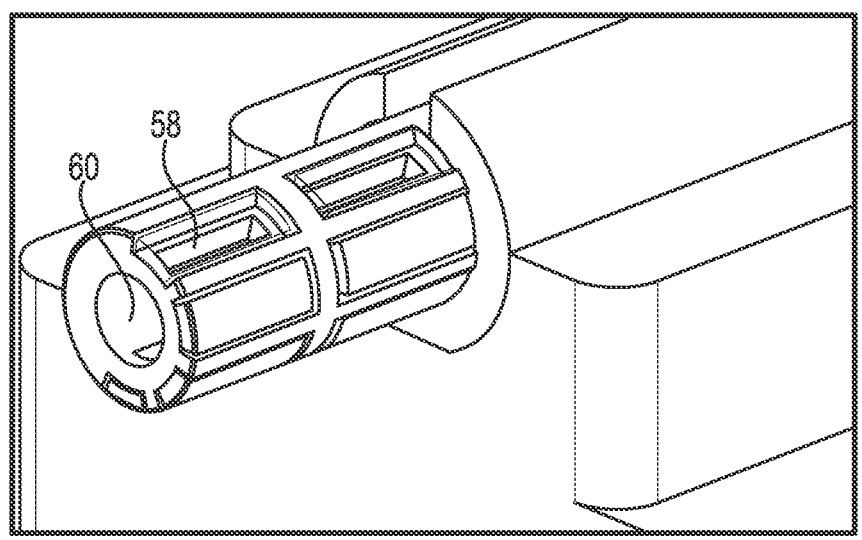

In the embodiment of the test fixture 50 illustrated in FIGS. 3A and 3B, the base is a two-portion mandrel 52 with an optional groove 54 cut out of an exterior portion, similar to the slot 21a of FIG. 2A, for clocking the neuromodulation device within the test fixture 50. The interior portion of the mandrel 52 includes a number of conductive pads 56, each of which may be positioned and press fit or adhered within a cutout 58 of the interior portion of the mandrel. The cutouts 58 under the conductive pads 56 may allow for more wire routing space. Wires (not shown in FIGS. 3A and 3B) my either be soldered, or laser welded onto the underside of the conductive pad 56 prior to the conductive pad being adhered onto the mandrel 52. The center 60 of the mandrel 52 may also be hollow to allow for a wire routing path through the front and back of the mandrel. The number of conductive pads 56 is based on the configuration of the test fixture 50 and the neuromodulation device to be tested.

The surface area of the conductive pads 56 may be machined out of a smooth (i.e., non-abrasive) metal and shaped and sized to optimize contact with the electrodes while reducing abrasion to the surface material of the electrodes. The conductive pads 56 may be coated with a contact-grade plating, such as 99% purity gold plating, electroless nickel plating, or silver plating, but any suitable conductive plating may be sufficient. The interior portion of the mandrel 52 may be oversized compared to the interior diameter of the neuromodulation device to be tested in order to ensure better contact between the conductive pads 56 and the electrode surfaces. The amount by which the mandrel may be oversized may be approximately 2-3 mm and/or between approximately 35-40% larger than the neuromodulation device to be tested. Oversizing the mandrel relative to the neuromodulation device may result in a contact force between the overstretched neuromodulation device and the conductive pads of the test fixture.

In an embodiment, the individual conductive pads may be formed from exposed smooth metallic areas of a flex circuit. The flex circuit may be formed of a flexible plastic substrate, such as polymide, PEEK or a transparent conductive polyester film. The metallic areas of the conductive pads and the corresponding wiring may be printed, photolithographically applied, or adhered, such as very thin copper strips adhered between two layers of the substrate and exposed in areas corresponding to the conductive pads. All of the materials may be coated with contact grade plating or other suitable plating post-fabrication to be biocompatible. Wiring traces from the conductive pads may lead to a lead with contacts that can be used to measure continuity or resistance between the different electrode locations. The flex circuit may then be wrapped around a mandrel, such as that shown in FIGS. 3A and 3B, or used with other embodiments described herein. In an embodiment, the flex circuit may be wrapped around the oversized mandrel with pressure sensitive adhesive to ensure even pressure and contact between the metallic areas and the conductive pads.

Figure 4:
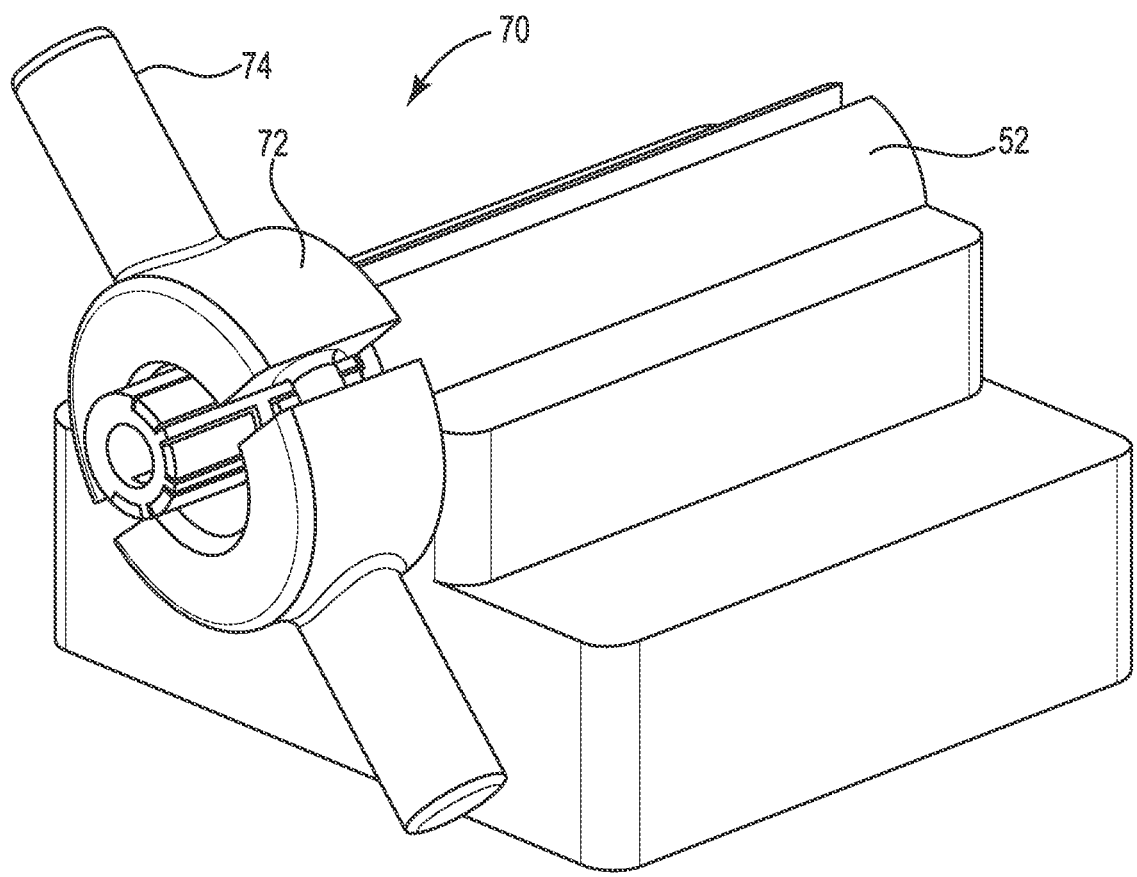
FIG. 4 is a perspective view a clamping tool configured for use with the test fixture of FIGS. 3A and 3B.

In an embodiment, further illustrated in FIG. 4, a clamping tool 70 may be used to help ensure sufficient, even contact between the conductive pads and the electrode surfaces. The clamping tool 70 may have a central portion 72 that may be positioned around the outer diameter of the neuromodulation device (not shown in FIG. 4 to simplify the illustration). As illustrated, the central portion 72 is in the form of two C-clamps that may be brought toward one another by screws 74 to apply even pressure to the neuromodulation device. The clamping tool 70 is illustrated in FIG. 4 with the test fixture illustrated in FIGS. 3A and 3B but could be readily used with the test fixture of FIGS. 2A and 2B, or the flex circuit described above, or with other embodiments.

Figure 5:
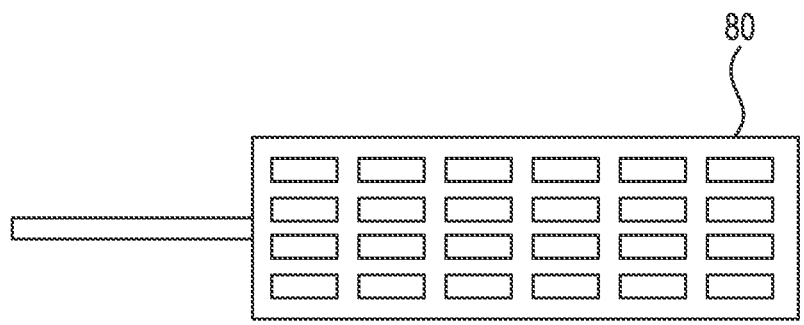
FIG. 5 is a perspective view of a flat neuromodulation device.
Figure 6:
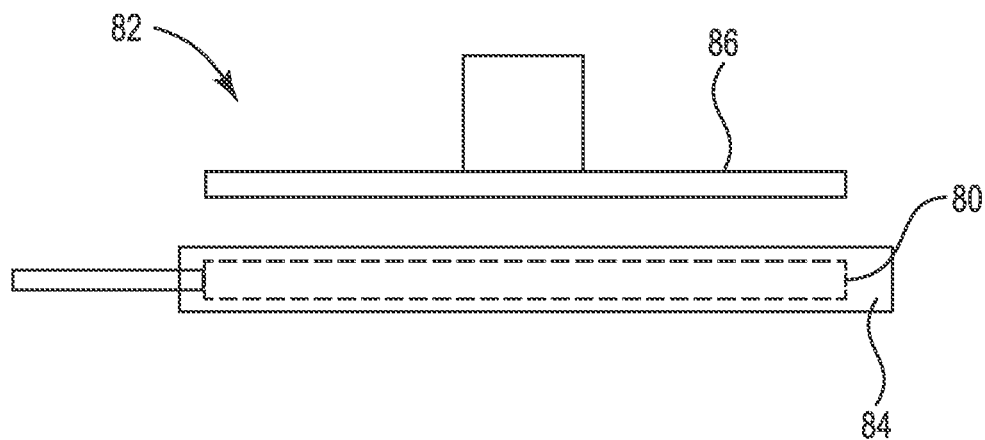
FIG. 6 is a side view illustration of a test fixture for a flat neuromodulation device, such as one shown in FIG. 5.

In an embodiment illustrated in FIGS. 5 and 6, the same concepts described herein can be applied to neuromodulation devices that are not cuff-like, such as the flat, paddle-like neuromodulation device 80 illustrated in FIG. 5. The neuromodulation device 80 is similar in construction to the other neuromodulation devices described herein, only the substrate in which the electrodes are positioned is flat or substantially flat, and the device may include a larger number of electrodes, sensors, or arrays. Although this type of neuromodulation device 80 may be wrapped around the test fixtures described above, bending the device 80 in that manner might damage the electrodes or the wiring inside the device. According, a different test fixture, based on the same concepts described herein, may be used, such as the test fixture 82 illustrated in FIG. 6, which may comprise a test bed 84 within which the neuromodulation device 80 may be placed and a retention device 86 that may be placed on top of the neuromodulation device 80. The test bed 84 may include conductive pads as described herein. The retention device 86 may supply slight pressure to the back of the neuromodulation device 80 sufficient to ensure contact between the conductive pads and the electrodes of the neuromodulation device 80.

In accordance with the foregoing disclosure, a method for performing electrical continuity testing of an implantable lead cuff 10 comprises the steps of providing a test fixture 20 of the kind described above. Next, the cuff may be coupled to the test fixture by inserting the probe into an interior portion of the cuff such that electrodes in portions of the cuff contact the pads. Or the paddle may be inserted into a test bed and retained therein so that the electrodes of the paddle contact the pads. Probes of a metering device may then be electrically coupled to the conductive wires of the test fixture connected to the pads. Finally, the electrical continuity of the cuff/paddle may be measured with the metering device.

In addition to or as an alternative to the above, the following examples consistent with the present teachings are set out in the following numbered clauses:

1. A test fixture (20) for testing electrical continuity in an electrode of a neuromodulation device, comprising:
 a substrate (22);
 an electrically conductive pad (24a) disposed on the substrate for reducing pressure applied to the electrode when the electrically conductive pad makes contact with an exposed surface of the electrode; and
 a wire (26a) extending from the electrically conductive pad.

2. The test fixture of clause 1, wherein the electrically conductive pad is non-abrasive to the exposed surface of the electrode.

3. The test fixture of clause 2, wherein the electrically conductive pad is at least formed of a conductive foam on a surface contacting the exposed surface of the electrode.

4. The test fixture of clause 2, wherein the electrically conductive pad is at least formed of a smooth metal on a surface contacting the exposed surface of the electrode.

5. The test fixture of clause 1, wherein the substrate comprises a probe having walls
 forming a slot in which the electrically conductive pad is affixed, and wherein the wire is positioned in the slot beneath the electrically conductive pad.

6. The test fixture of clause 5, wherein the neuromodulation device is a cuff-like device that is configured to wrap around the probe so that the electrically conductive pad is in contact with the electrode.

7. The test fixture of clause 6, wherein the probe is mounted on a base that is configured to align the electrically conductive pad with the electrode.

8. The test fixture of clause 1, further comprising a clamp configured to apply pressure to the neuromodulation device sufficient to ensure contact between the electrically conductive pad and the electrode.

9. The test fixture of clause 1, wherein the substrate comprises a mandrel.

10. The test fixture of clause 9, wherein the mandrel forms an opening in which the electrically conductive pad is affixed, and wherein the wire is positioned in the opening beneath the electrically conductive pad.

11. The test fixture of clause 10, wherein the mandrel includes a central opening configured to provide routing space for the wire.

12. The test fixture of clause 9, wherein the neuromodulation device is a cuff-like device that is configured to wrap around the mandrel so that the electrically conductive pad is in contact with the electrode, and wherein an exterior diameter of the mandrel is radially oversized relative to an interior diameter of the cuff-like device.

13. The test fixture of clause 12, wherein the mandrel is radially oversized by approximately 35-40 percent.

14. The test fixture of clause 9, wherein the mandrel is mounted on a base that is configured to align the electrically conductive pad with the electrode.

15. The test fixture of clause 1, wherein the substrate is a flexible plastic and wherein the electrically conductive pad is an exposed smooth metallic area on or within the flexible plastic.

16. The test fixture of clause 1, wherein the substrate and the neuromodulation device are substantially flat, further comprising a retention device configured to apply pressure to the neuromodulation device sufficient to ensure contact between the electrically conductive pad and the electrode.

17. The test fixture of clause 1, wherein the wire is configured to be electrically coupled to a multimeter for continuity measurements of the electrode.

18. A method for performing electrical continuity testing of a neuromodulation device (10), comprising:
providing a test fixture (20), the text fixture comprising:
a substrate (22);
an electrically conductive pad (24a) disposed on the substrate for reducing pressure applied to the electrode when the electrically conductive pad makes contact with an exposed surface of the electrode; and
a wire (26a) extending from the electrically conductive pad;
coupling the neuromodulation device to the test fixture such that the electrically conductive pad is in electrical contact with the electrode; and
electrically coupling probes of a metering device to the wire and measuring electrical continuity of the electrode and wire.

19. The method of clause 18, wherein the electrically conductive pad is non-abrasive to the exposed surface of the electrode.

20. The method of clause 19, wherein the electrically conductive pad is at least formed of a conductive foam on a surface contacting the exposed surface of the electrode.

21. The method of clause 19, wherein the electrically conductive pad is at least formed of a smooth metal on a surface contacting the exposed surface of the electrode.

22. The method of clause 18, wherein the substrate comprises a probe having walls forming a slot in which the electrically conductive pad is affixed, and wherein the wire is positioned in the slot beneath the electrically conductive pad.

23. The method of clause 22, wherein the neuromodulation device is a cuff-like device, further comprising wrapping the cuff-like device around the probe so that the electrically conductive pad is in contact with the electrode.

24. The method of clause 23, wherein the probe is mounted on a base, further comprising positioning the cuff-like device relative to the base to align the electrically conductive pad with the electrode.

25. The method of clause 18, further comprising applying a clamping tool around the neuromodulation device to apply pressure to the neuromodulation device sufficient to ensure contact between the electrically conductive pad and the electrode.

26. The method of clause 18, wherein the substrate comprises a mandrel.

27. The method of clause 26, wherein the mandrel forms an opening in which the electrically conductive pad is affixed, and wherein the wire is positioned in the opening beneath the electrically conductive pad.

28. The method of clause 27, wherein the mandrel includes a central opening configured to provide routing space for the wire.

29. The method of clause 26, wherein the neuromodulation device is a cuff-like device, further comprising wrapping the cuff-like device around the mandrel so that the electrically conductive pad is in contact with the electrode, and wherein an exterior diameter of the mandrel is radially oversized relative to an interior diameter of the cuff-like device.

30. The method of clause 29, wherein the mandrel is radially oversized by approximately 35-40 percent.

31. The method of clause 26, wherein the mandrel is mounted on a base, further comprising positioning the cuff-like device relative to the base to align the electrically conductive pad with the electrode.

32. The method of clause 18, wherein the substrate is a flexible plastic and wherein the electrically conductive pad is an exposed smooth metallic area on or within the flexible plastic.

33. The method of clause 1, wherein the substrate and the neuromodulation device are substantially flat, further comprising applying pressure to the neuromodulation device sufficient to ensure contact between the electrically conductive pad and the electrode.

The foregoing description of the examples, including illustrated examples, of the disclosure has been presented only for the purpose of illustration and description and is not intended to be exhaustive or to limit the invention to the precise forms disclosed. Numerous modifications, adaptations, and uses thereof will be apparent to those skilled in the art without departing from the scope of this invention. The illustrative examples described above are given to introduce the reader to the general subject matter discussed here and are not intended to limit the scope of the disclosed concepts.

What is claimed:

1. A test device for testing electrical continuity in an electrode of a neuromodulation device, comprising:
a substrate;
an electrically conductive pad disposed on the substrate for contacting the electrode; and
a wire extending from the electrically conductive pad, wherein the electrically conductive pad is configured to reduce pressure applied to the electrode when the electrically conductive pad makes contact with an exposed surface of the electrode, and wherein the neuromodulation device is arranged to wrap around the substrate.

2. The test device of claim 1, wherein the electrically conductive pad is non-abrasive to the exposed surface of the electrode.

3. The test device of claim 1, wherein the electrically conductive pad is at least formed of a conductive foam on a surface contacting the exposed surface of the electrode.

4. The test device of claim 3, wherein the neuromodulation device is a cuff-like device that is configured to wrap around the substrate so that the electrically conductive pad is in contact with the electrode.

5. The test device of claim 1, wherein the electrically conductive pad is at least formed of a smooth metal on a surface contacting the exposed surface of the electrode.

6. The test device of claim 1, wherein the substrate comprises a probe having walls forming a slot in which the electrically conductive pad is affixed, and wherein the wire is positioned in the slot beneath the electrically conductive pad.

7. The test device of claim 1, further comprising a clamp configured to apply pressure to the neuromodulation device sufficient to ensure contact between the electrically conductive pad and the electrode.

8. The test device of claim 1, wherein the substrate comprises a mandrel.

9. The test device of claim 8, wherein the mandrel forms an opening in which the electrically conductive pad is affixed, and wherein the wire is positioned in an opening beneath the electrically conductive pad.

10. The test device of claim 8, wherein the mandrel includes a central opening configured to provide routing space for the wire.

11. The test device of claim 8, wherein the neuromodulation device is a cuff-like device that is configured to wrap around the mandrel so that the electrically conductive pad is in contact with the electrode, and wherein an exterior diameter of the mandrel is radially oversized relative to an interior diameter of the cuff-like device.

12. The test device of claim 11, wherein the mandrel is radially oversized by approximately 35-40 percent.

13. The test device of claim 8, wherein the mandrel is mounted on a base that is configured to align the electrically conductive pad with the electrode.

14. The test device of claim 1, wherein the substrate is a flexible plastic and wherein the electrically conductive pad is an exposed smooth metallic area on or within the flexible plastic.

15. The test device of claim 1, wherein the substrate and the neuromodulation device are substantially flat, further comprising a retention device configured to apply pressure to the neuromodulation device sufficient to ensure contact between the electrically conductive pad and the electrode.

16. The test device of claim 1, wherein the wire is configured to be electrically coupled to a multimeter for continuity measurements of the electrode.

17. A test device for testing electrical continuity in an electrode of a neuromodulation device, comprising:
   a substrate;
   an electrically conductive portion disposed on the substrate,
   wherein the substrate comprises a probe configured for the neuromodulation device to wrap around such that the electrically conductive portion is in contact with the electrode; and
   a wire extending from the electrically conductive portion, wherein the electrically conductive portion is configured to reduce pressure applied to the electrode when the electrically conductive portion makes contact with an exposed surface of the electrode.

18. The test device of claim 17, wherein the electrically conductive portion comprises an electrically conductive pad.

19. The test device of claim 17, wherein the probe is mounted on a base that is configured to align the electrically conductive portion with the electrode.

20. The test device of claim 17, wherein the probe comprises a substantially cylindrical shape.

21. A method for performing electrical continuity testing of a neuromodulation device comprising an electrode, comprising:
   providing a test device, the test device comprising:
      a substrate;
      an electrically conductive portion disposed on the substrate; and
      a wire extending from the electrically conductive portion;
   coupling the neuromodulation device to the test device such that the neuromodulation device wraps around the substrate and the electrically conductive portion is in electrical contact with the electrode; and
   electrically coupling probes of a metering device to the wire and measuring electrical continuity of the electrode and wire, wherein the electrically conductive portion is configured to reduce pressure applied to the electrode when the electrically conductive portion makes contact with an exposed surface of the electrode.

* * * * *